United States Patent
Hasegawa

(10) Patent No.: US 7,087,074 B2
(45) Date of Patent: Aug. 8, 2006

(54) LIGHT THERAPY APPARATUS

(75) Inventor: Motoharu Hasegawa, Tokyo (JP)

(73) Assignee: Institute of Medical Information System Co., Ltd., Tokyo (JP)

( * ) Notice: Subject to any disclaimer, the term of this patent is extended or adjusted under 35 U.S.C. 154(b) by 290 days.

(21) Appl. No.: 10/437,010

(22) Filed: May 14, 2003

(65) Prior Publication Data

US 2003/0216796 A1 Nov. 20, 2003

(30) Foreign Application Priority Data

May 17, 2002 (JP) ........................................ 2002-143298

(51) Int. Cl.
*A61N 5/06* (2006.01)

(52) U.S. Cl. .......................................... 607/88; 607/90

(58) Field of Classification Search ...................... 606/9; 607/88–94
See application file for complete search history.

(56) References Cited

U.S. PATENT DOCUMENTS

| | | | | | |
|---|---|---|---|---|---|
| 4,106,857 | A | * | 8/1978 | Snitzer | 359/885 |
| 4,487,478 | A | * | 12/1984 | Jackson | 359/601 |
| 5,043,571 | A | * | 8/1991 | Hasegawa | 250/226 |
| 5,574,286 | A | * | 11/1996 | Huston et al. | 250/372 |
| 5,843,143 | A | * | 12/1998 | Whitehurst | 607/88 |
| 6,280,438 | B1 | * | 8/2001 | Eckhouse et al. | 606/9 |
| 6,290,713 | B1 | * | 9/2001 | Russell | 607/88 |
| 6,676,655 | B1 | * | 1/2004 | McDaniel | 606/9 |
| 2003/0004556 | A1 | * | 1/2003 | McDaniel | 607/88 |
| 2003/0035301 | A1 | * | 2/2003 | Gardiner et al. | 362/583 |
| 2003/0151819 | A1 | * | 8/2003 | Pong et al. | 359/582 |

OTHER PUBLICATIONS

Fukunori Hattori et al., "Therapeutic Efficacy of Irradiation with an Artificial Solar Illumination Lamp on Pressure Ulcer Infected Areas" –A three–institute joint clinical study–.

* cited by examiner

*Primary Examiner*—Roy D. Gibson
*Assistant Examiner*—Henry M Johnson, III
(74) *Attorney, Agent, or Firm*—Shoemaker and Mattare

(57) ABSTRACT

This invention discloses a light therapy apparatus which has a curing effect by means of light irradiation and which less stimulates an irradiated portion. The light therapy apparatus according to this invention has a light source (2) and a spectrofilter (5) for substantially blocking, of spectrum components of light emitted from the light source (2), those other than a spectrum component within a predetermined range, and radiates light transmitted through the filter. The spectrofilter (5) has characteristics of transmitting a first wavelength component having a wavelength of about 280 nm to 400 nm and a second wavelength component having a wavelength of not less than about 700 nm, while substantially blocking a wavelength component at least between the first and second wavelength components.

7 Claims, 4 Drawing Sheets

LIGHT THERAPY APPARATUS

FIELD OF THE INVENTION

The present invention relates to a light therapy apparatus and, more particularly, to a light therapy apparatus which emits light having a specific wavelength component.

BACKGROUND OF THE INVENTION

Various studies have conventionally been made on the influence of light, particularly sunlight, on human health. For example, it is reported that sunlight irradiation is effective against skin diseases such as a bedsore.

In the natural environment, however, the sunlight can be utilized only on sunny days and at sunny places, and its intensity differs largely depending on the season and time. In order to obtain the effect of sunlight regardless of the weather or location and with a predetermined intensity, a light therapy apparatus has been developed which emits pseudo-sunlight having a spectral distribution similar to that of sunlight.

The conventional light therapy apparatus has a spectral intensity almost coinciding with that of sunlight even in a visible light range (about 400 nm to 740 nm), and accordingly provides strong stimulation to the optic nerve and eyeball surface. It is therefore unpreferable to stare at an irradiation region or light source for long period of time. In particular, a wavelength in a near infrared range causes a burn and dryness in the surface of the irradiation region, and is accordingly unpreferable to treat a patient who does not like sunburn or an affected part with a disease such as a bedsore which should not be dried.

Also, a specific wavelength range cannot be selectively extracted and utilized, and its intensity cannot be changed.

SUMMARY OF THE INVENTION

The present invention has been made in view of the problems of the prior art, and has as its object to provide a light therapy apparatus which has a curing effect by means of light irradiation and which less stimulates the retina.

It is another object of the present invention to provide a light therapy apparatus in which the wavelength range to be radiated and the intensity can be selected.

The present inventors conducted extensive studies to achieve the above objects, and found that, of the spectral distribution of sunlight, the wavelength components that work effectively to treat skin diseases are the first component of about 280 nm to 400 nm and the second wavelength component of about 700 nm or more, thus reaching the present invention.

More specifically, the gist of the present invention resides in a light therapy apparatus which has a light source and a filter for substantially blocking, of spectrum components of light emitted from the light source, those other than a spectrum component within a predetermined range, and which radiates light transmitted through the filter, wherein the filter has characteristics of transmitting a first wavelength component having a wavelength of about 280 nm to 400 nm and a second wavelength component having a wavelength of not less than about 700 nm, while substantially blocking a wavelength component at least between the first and second wavelength components.

Another gist of the present invention resides in a light therapy apparatus which has a plurality of light sources and a plurality of filters for substantially blocking, of spectrum components of light emitted from the plurality of light sources, those other than a spectrum component within a predetermined range, and which radiates light transmitted through the plurality of filters for substantially the same treatment region, wherein the plurality of filters have characteristics of transmitting at least one of a first wavelength component having a wavelength of about 280 nm to 400 nm and a second wavelength component having a wavelength of not less than about 700 nm and substantially blocking a wavelength component at least between the first and second wavelength components, and are used in such a combination that a wavelength component of the light to be radiated includes the first and second wavelength components.

Further objects, features and advantages of the present invention will become apparent from the following detailed description of embodiments of the present invention with reference to the accompanying drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

Preferred embodiments of the present invention will now be described in detail in accordance with the accompanying drawings.

(First Embodiment)

Figure 1:
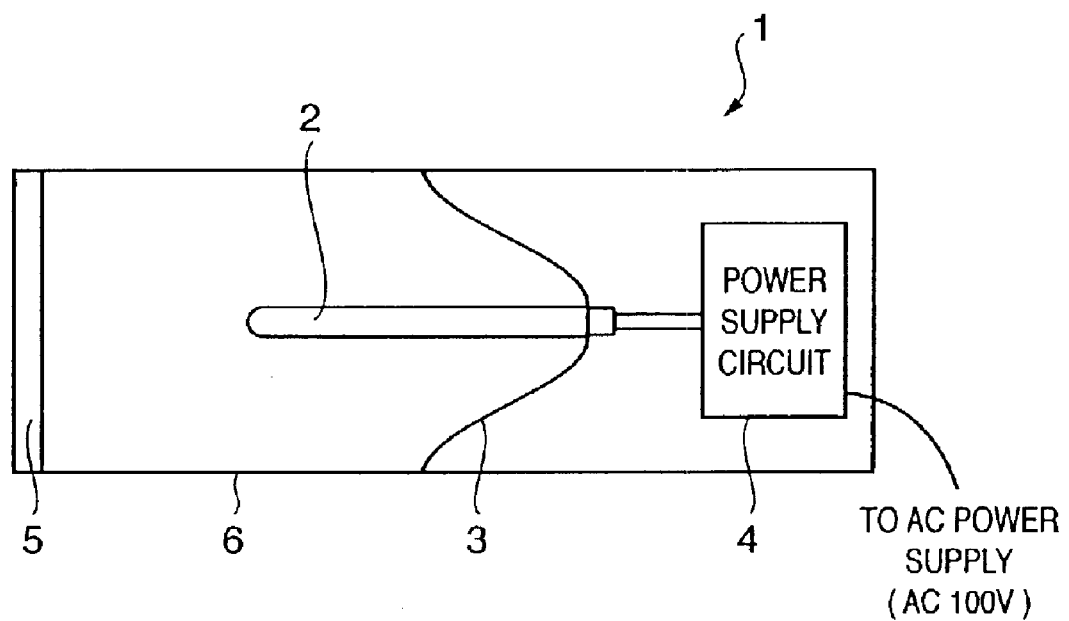
FIG. 1 is a view showing the arrangement of the main part of a light therapy apparatus according to the first embodiment of the present invention.

FIG. 1 is a vertically sectional view showing an arrangement of a light therapy apparatus according to the first embodiment of the present invention.

Referring to FIG. 1, a light therapy apparatus 1 has a xenon lamp 2, reflecting plate 3, power supply circuit 4, spectrofilter 5, and cylindrical main body 6. FIG. 1 shows only the basic arrangement of the light therapy apparatus according to the present invention. Actually, the light therapy apparatus 1 may also have a pan head and stand for supporting the main body 6 and adjustably maintaining the light radiation direction in a desired direction, a fan for promoting heat dissipation of the lamp 2, a lens for controlling the light irradiation range, and the like. The power supply circuit 4 may be incorporated in the main body 6 or be provided outside the main body 6.

The arrangement and type of the xenon lamp 2 are arbitrary, but those with little brightness and long lifetime are preferable. The power supply circuit 4 includes circuits necessary for stably controlling the xenon lamp 2, e.g., a ballast for rectifying a commercial AC power to a DC current, a starter for generating an RF high voltage suitable for starting the xenon lamp 2 as a discharge lamp and for causing dielectric breakdown between the electrodes, and the like.

The reflecting plate 3 has a funnel-like shape. If the xenon lamp 2 is to be used in the vertical direction, the reflecting plate 3 is arranged such that the xenon lamp 2 extends through its center.

In any case, the light therapy apparatus according to the present invention is characterized in its output wavelength. Regarding the xenon lamp 2 and an arrangement for turning it on, products that can be commercially available can be appropriately selected and used.

The spectrofilter 5 characterizes the light therapy apparatus according to this embodiment the most, and has the following characteristics. Of the continuous spectra of from the ultraviolet range to infrared range (about 200 nm to 2,500 nm or more) of the xenon lamp 2, the spectrofilter 5 substantially transmits the first wavelength component of about 280 nm to 400 nm and the second wavelength component of about 700 nm or more, preferably about 700 nm to 2,500 nm and more preferably about 700 nm to 1,000 nm, and substantially blocks light of other spectrum ranges, particularly at least the main portion of a visible light range (about 400 nm to 750 nm).

Of these wavelength components, the first wavelength component directly acts on the cells and has a function of activating cell functions and synthesizing matters. The second wavelength component activates the cells of the irradiated portion with its infrared radiation energy and supplies them a temperature (about 37° C. or more) necessary for promoting reaction. When these wavelength components are used in combination, a therapeutic effect by light irradiation can be obtained while suppressing adverse influence of the visible light on eyes.

The effects of these wavelengths are indicated in, e.g., Utsunomiya Yoshimasa, "Light Therapy", Kenkou to Kousen Sha, Kuroda Yasujirou, "visible Light Therapy: Heredity and Light" The Light Laboratory Foundation, and the like.

The upper and lower limits of each of the first and second wavelength components radiated by the light therapy apparatus of the present invention do not necessarily block 100% of wavelength components higher than the upper limit or lower than the lower limit. This is because the transmitting/blocking characteristics of the spectrofilter 5 as an optical filter do not have a rectangular form but generally form a curve indicating that the transmittance decreases stepwisely as the wavelength deviates from the wavelength for which the filter has a maximum transmittance.

Therefore, the first wavelength component mainly has a wavelength component of about 280 nm to 400 nm, but may also have a wavelength of up to about 450 nm on the long wavelength side. A wavelength component of less than 280 nm is preferably blocked completely as it is regarded harmful.

The second wavelength component also mainly has a wavelength component of about 700 nm or more, particularly preferably about 700 nm to 2,500 nm and more preferably about 700 nm to 1,000 nm, but may include a wavelength component of about 700 nm ±50 nm on the short wavelength side and a wavelength component of ±50 nm on the long wavelength side.

The visible light range (about 400 nm to 750 nm) need not be blocked 100%. It suffices as far as light of the main portion of the visible light range is transmitted with a sufficiently low transmittance of, e.g., less than 10%, preferably less than 5%.

Figure 2:
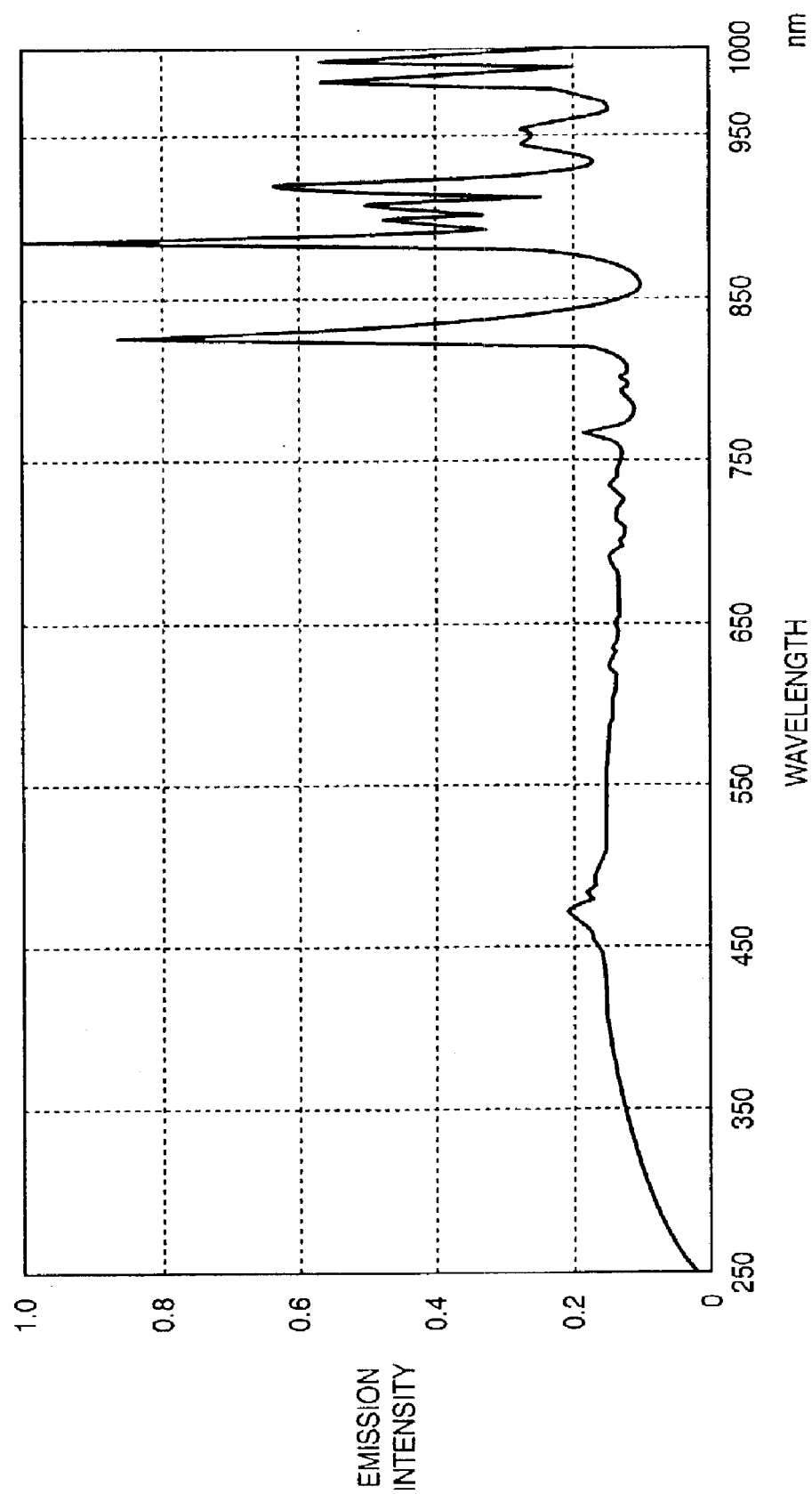
FIG. 2 is a graph showing an example of the light emission spectrum characteristics of a xenon lamp as a lamp that can be utilized as the light source of the light therapy apparatus according to the present invention.
Figure 3:
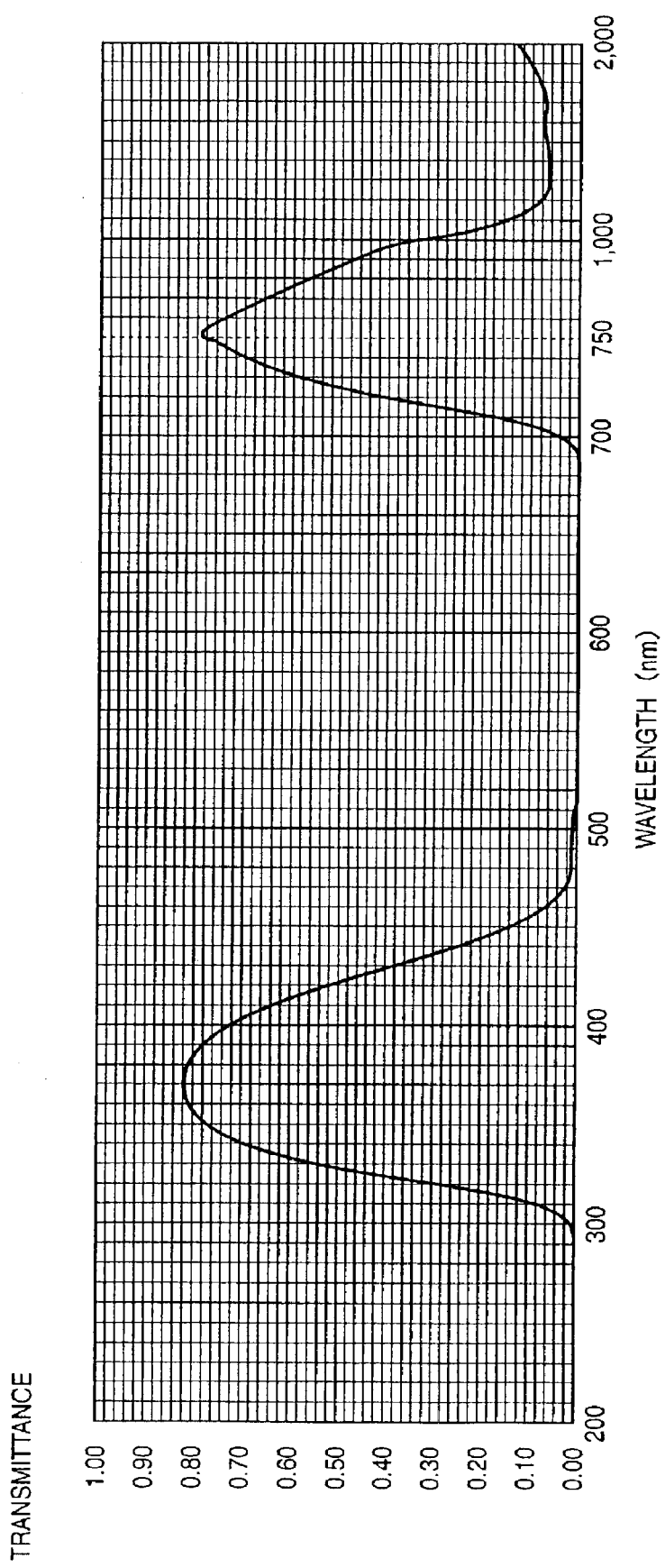
FIG. 3 is a graph showing an example of the transmission characteristics of a filter that can be utilized as a spectrofilter 5 of the first embodiment.

FIG. 2 is a graph showing an example of spectrum characteristics of a xenon lamp that can be used in the light therapy apparatus according to the present invention, and FIG. 3 is a graph showing the transmission characteristics of an optical filter that can be used as a spectrofilter of this embodiment.

When the light therapy apparatus having this arrangement is to be actually used, irradiation is performed at such a distance that the temperature of the light-irradiated portion becomes 37° C. or more and the light-irradiated portion does not cause a burn even when it is irradiated continuously for a predetermined period of time (e.g., two hours or more). Strictly, the temperature is the tissue temperature of the portion that is to be treated, and does not necessarily indicate the temperature of the skin surface. This is because the deep portion warming effect obtained by adjusting the second wavelength component exhibits its warming effect not on the skin surface but under the skin.

Irradiation is performed at a distance satisfying these temperature conditions because, in order to effectively utilize the function of the first wavelength component against cells, a temperature of 37° C., which is appropriate for cell reaction, may be necessary. A timer circuit (not shown) or the like may be provided, so irradiation is ended at a preset time.

More specifically, when a 100-Watt (Volt-Ampere) xenon lamp is used, irradiation can be performed at a distance of about 70 cm.

The spectrofilter that can be used in this embodiment can have any arrangement as far as it has the characteristics described above. For example, a filter obtained by coating a base such as glass with a single or multiple layers of thin films by vacuum deposition, a filter formed by mixing a specific material in the material itself of the filter (filter formed by electromagnetic wave absorption scheme), a filter obtained by further coating, with a thin film, a filter formed by electromagnetic absorption, or the like can be used. To obtain a filter having the above transmission characteristics with the above arrangements is known in the field of optical filter manufacture, and no further description thereof will be made.

(Modification of First Embodiment)

According to the transmission characteristics of the spectrofilter 5 shown in FIG. 3, the spectrofilter 5 shows almost the same transmittance for both the first and second wavelength components. If a spectrofilter 5 having a different transmittance ratio of the first wavelength component to the second wavelength component is used, the effects of the respective wavelength components can be controlled.

For example, a plurality of types of spectrofilters having a constant transmittance for the second wavelength component and different transmittances for the first wavelength component which acts on the cells may be selectively used in accordance with the symptoms and the curing state. When the irradiation distance is short and the temperature of the irradiated portion increases excessively, a spectrofilter in which the transmittance for the second wavelength component is decreased may be used.

If the spectrofilter 5 is attached to the main body 6 by screwing, it can be changed easily as in an ordinary camera.

In this manner, according to this embodiment, a light therapy apparatus can be realized which has a curing effect obtained by light irradiation and which can prevent adverse affects such as dryness or burn of the irradiated portion caused by visible light.

(Second Embodiment)

In the first embodiment, an optical therapy apparatus using one radiation body is proposed. The second embodiment is characterized in that an optical therapy apparatus is formed by using a plurality of radiation bodies.

Figure 4:
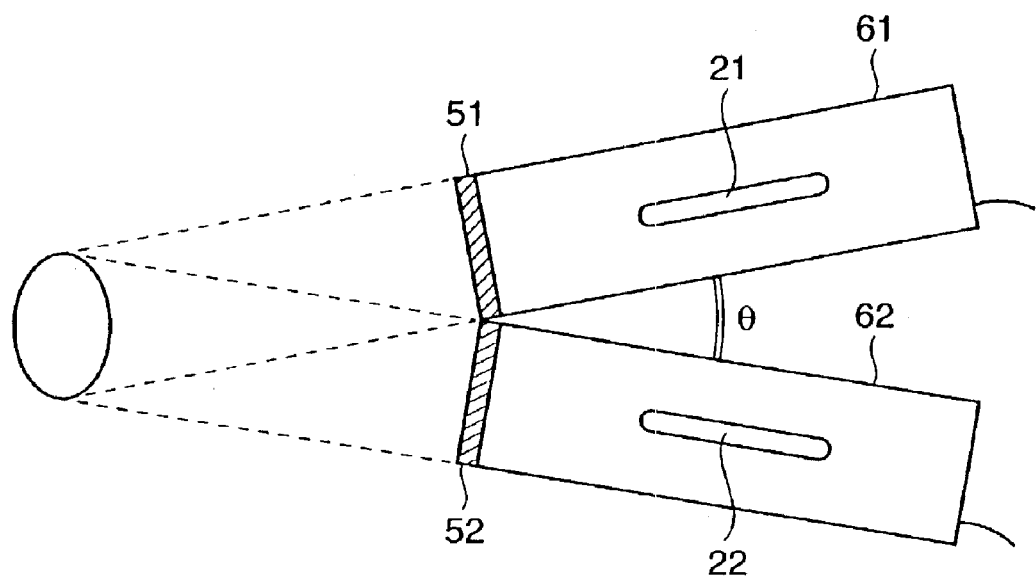
FIG. 4 is a view showing the arrangement of the main part of a light therapy apparatus according to the second embodiment of the present invention.

FIG. 4 is a schematic view showing an arrangement of a light therapy apparatus according to this embodiment. The light therapy apparatus shown in FIG. 4 is obtained by connecting two light therapy apparatuses each having the same arrangement as that of FIG. 1 described in the first embodiment, and its basic arrangement is the same as that of the first embodiment. In the second embodiment, constituent elements that are not particularly changed are omitted.

Note that the second embodiment is characterized in that it can be controlled more flexibly than the light therapy apparatus of the first embodiment by selecting the characteristics of spectrofilters 51 and 52 and xenon lamps 21 and 22 in various manners.

Main bodies 61 and 62 are supported to form an angle θ so that their irradiation regions coincide with each other at predetermined irradiation distances. This angle θ can be adjusted in accordance with the irradiation distance.

For example, the spectrofilter 51 may have the same characteristics as those shown in FIG. 3 for a region of 200 nm to 600 nm, and may substantially block light in a long wavelength range of 600 nm or more. The spectrofilter 52 may have the same transmission characteristics as those shown in FIG. 3 for the long wavelength range of 600 nm or more, and may substantially block light in a short wavelength range of less than 600 nm. Then, the main bodies 61 and 62 respectively radiate the first and second wavelength components independently of each other.

Therefore, when the characteristics, e.g., wattage, of the xenon lamps 21 and 22 are differed, the intensities of the first and second wavelength components can be controlled independently of each other. Alternatively, the intensities may be controlled by controlling the lamp driving method independently.

Alternatively, outputs from the xenon lamps 21 and 22 may be set equal. The spectrofilter 51 may have the same characteristics as those of the spectrofilter 5 of the first embodiment. The spectrofilter 52 may have such transmission characteristics that it transmits only the first or second wavelength component. The intensities of the respective wavelength components can be controlled independently of each other with this arrangement.

In the second embodiment as well, the spectrofilters 51 and 52 can be changed, as described in the modification of the first embodiment.

Three or more main bodies may be used.

In the above embodiments, a xenon lamp is used as the light source. The gist of the present invention is to radiate light having the first wavelength component and that having the second wavelength component, as described above. Any other arbitrary light source can be used as far as it includes these wavelength components in its light spectrum.

In particular, when a plurality of lamps are used as in the second embodiment, a lamp having light spectrum characteristics including only one of the first and second wavelength components can be used as each of the xenon lamps 21 and 22.

As has been described above, according to the present invention, a light therapy apparatus can be realized which has a curing effect obtained by light irradiation, which less stimulates the eyes, and which can prevent a burn or dryness of the diseased part.

Furthermore, the present invention can be applied to the system comprising either a plurality of units or a single unit. It is needless to say that the present invention can be applied to the case which can be attained by supplying programs which execute the process defined by the present system or invention.

The present invention is not limited to the above embodiments and various changes and modifications can be made within the sprit and scope of the present invention. Therefore, to apprise the public of the scope of the present invention the following claims are made.

What is claimed is:

1. A light therapy apparatus which has a light source, and a filter for substantially blocking, of spectrum components of light emitted from said light source, those other than a spectrum component within a predetermined range, and which radiates light transmitted through said filter, wherein said filter has characteristics of transmitting a first wavelength component having a wavelength of about 280 nm to 400 nm and a second wavelength component having a wavelength of not less than about 700 nm, while substantially blocking a wavelength component at least between the first and second wavelength components.

2. The apparatus according to claim 1, wherein a transmittance for the first wavelength component of said filter and a transmittance for the second wavelength component thereof are different from each other.

3. The apparatus according to claim 1, wherein said light source is a xenon lamp.

4. A light therapy apparatus which has a plurality of light sources, and a plurality of filters for substantially blocking, of spectrum components of light emitted from said plurality of light sources, those other than a spectrum component within a predetermined range, and which radiates light transmitted through said plurality of filters for substantially a same treatment region, wherein said plurality of filters have characteristics of transmitting at least one of a first wavelength component having a wavelength of about 280 nm to 400 nm and a second wavelength component having a wavelength of not less than about 700 nm, while substantially blocking a wavelength component at least between the first and second wavelength components, and are used in such a combination that a wavelength component of the light to be radiated includes the first and second wavelength components.

5. The apparatus according to claim 4, wherein said plurality of light sources include light sources having different output intensities.

6. The apparatus according to claim 4, wherein a transmittance for the first wavelength component of a filter, among said plurality of filters, which transmits both the first and second wavelength components, and a transmittance for the second wavelength component thereof are different from each other.

7. The apparatus according to claim 4, wherein said plurality of light sources comprise two light sources, said plurality of filters comprise two filters, and one of said two filters transmits only the first wavelength component while the other filter thereof transmits only the second wavelength component.

* * * * *

UNITED STATES PATENT AND TRADEMARK OFFICE
CERTIFICATE OF CORRECTION

PATENT NO. : 7,087,074 B2
APPLICATION NO. : 10/437010
DATED : August 8, 2006
INVENTOR(S) : Hasegawa It is certified that error appears in the above-identified patent and that said Letters Patent is hereby corrected as shown below:

On the title page in the second column, in the References Cited, item (56) entitled OTHER PUBLICATIONS should include the following:

-- Y. Utsunomiya et al., "Light Therapy", Kenkou to Kousen Sha, 1988.10, pp. 21-26; with English translation Y. Kuroda, "Visible Light Therapy: Heredity and Light", The Light Laboratory Foundation, 1997.2, pp. 105-107; with English translation --

Signed and Sealed this

Fifth Day of December, 2006

JON W. DUDAS
*Director of the United States Patent and Trademark Office*